United States Patent [19]
Tang et al.

[11] Patent Number: 6,001,607
[45] Date of Patent: Dec. 14, 1999

[54] HUMAN GROWTH-ASSOCIATED METHYLTRANSFEASES

[75] Inventors: Y. Tom Tang; Henry Yue, both of Sunnyvale; Karl J. Guegler, Menlo Park; Purvi Shah, Sunnyvale, all of Calif.

[73] Assignee: Incyte Pharmaceuticals, Inc., Palo Alto, Calif.

[21] Appl. No.: 09/059,522

[22] Filed: Apr. 13, 1998

[51] Int. Cl.$^6$ .............................. C12P 19/34; C12N 9/10; C12N 1/20; C07H 21/04

[52] U.S. Cl. .................. 435/91.1; 435/91.2; 435/193; 435/252.3; 435/320.1; 536/23.2

[58] Field of Search .............................. 435/252.3, 320.1, 435/193, 91.2, 91.1; 536/23.2

[56] References Cited

PUBLICATIONS

Gloria, L. et al., "DNA Hypomethylation and Proliferative Activity Are Increased in the Rectal Mucosa of Patients with Long–Standing Ulcerative Colitis", *Cancer*, 78: 2300–2306 (1996).

Turker, M.S. and T.H. Bestor, "Formation of methylation patterns in the mammalian genome", *Mutat. Res.*, 386: 119–130 (1997).

Bokar, J.A. et al., "Characterization and Partial Purification of mRNA N$^6$Adenosine Methyltransferase from HeLa Cell Nuclei", *J. Biol. Chem.*, 269: 17697–17704 (1994).

Willis, D.B. et al., "Transcription of Methylated Viral DNA by Eukaryotic RNA Polymerase II", *Cell, Biophys.*, 15: 97–111 (1989).

Weiss, B., "Cancer and the Dynamics of Neurodegenerative Processes", *Neurotoxicology*, 12: 379–386 (1991).

Collins, S.M. et al., "Effect of Inflammation of Enteric Nerves", *Ann. N.Y. Acad. Sci.*, 664: 415–424 (1992).

Brown, J.K. and H. Imam, "Interrelationships of Liver and Brain with Special Reference to Reye Syndrome",*J. Inherit. Metab Dis.*, 14: 436–458 (1991).

Kagan, R.M. and S. Clarke, "Widespread Occurrence of Three Sequence Motifs in Diverse S–Adenoslmethionine–Dependent Methyltransferases Suggests a Common Structure for These Enzymes", *Arch. Biochem. Biophys.*, 310: 417–427 (1994).

Rodriguez, I.R. et al., "Structural Analysis of the Human Hydroxyindole–O–methyltransferase Gene",*J. Biol. Chem.*, 269: 31969–31977 (1994).

Tenhunen, J. et al., "Genomic organization of the human catechol O–methyltransferase gene and its expression from two distinct promoters", *Eur. J. Biochem.*, 223: 1049–1059 (1994).

Bottiglieri, T. and K. Hyland, "S–adenosylmethionine levels in psychiatric and neurological disorders: a review", *Acta Neurol. Scand, Suppl.*, 154: 19–26 (1994).

Montgomery, J.A. et al., "Carbocyclic Analogue of 3–Deazaadenosine: A Novel Antiviral Agnet Using S–Adenosylhomocysteine Hydrolase as a Pharmacological Target", *J. Med. Chem.*, 25: 626–629 (1982).

Minarovits, J. et al., "Sequence–Specific Methylation Inhibits the Activity of the Epstein–Barr Virus LMP 1 and BCR2 Enhancer–Promoter Regions", *Virology*, 200: 661–667 (1994).

Boswami, B.B. et al., "2'–5'–Linked Oligo (adenylic Acid) and Its Analogs a New Class of Inhibitors of mRNA Methylation", *J. Biol. Chem.*, 257: 6867–6870 (1982).

Kramer, D.L. et al., "Combined Modulation of S–Adenosylmethionine Biosysthesis and S–Adenosylhomocysteine Methobolism Enhances Inhibition of Nucleic Acid Methylation an L1210 Cell Growth", *Cancer Res.*, 50: 3838–3842 (1990).

Avery, L. and H.R. Horvitz, "Effects of Starvation and Neuroactive Drugs on Feeding in *Caenorhabditis elegans*", *J. Ex. Zool.*, 253: 263–270 (1990).

McCance, K.L. and S.E. Huether, *Pathrophysiology*, Mosby–Year Book, Inc., St. Louis, MO, pp. 402–404 (1994).

Gundlach, A.L., "Disorder of the inhibitory glycine receptor: inherited myoclonus in Poll Hereford calves", *FASEB*, 4: 2761–2766 (1990).

Rodriguez, I.R. et al., (Direct Submission), GenBank Sequence Database (Accession U11088), National Center for Biotechnology Information, National Library of Medicine, Bethesda, Maryland, 20894, (GI 607843; GI 607854; GI 607855; 607853).

*Primary Examiner*—Rebecca E. Prouty
*Assistant Examiner*—Elizabeth Slobodyansky
*Attorney, Agent, or Firm*—Sheela Mohan-Peterson; Incyte Pharmaceuticals, Inc.

[57] ABSTRACT

The invention provides a human growth-associated methyltransferase (GAMT) and polynucleotides which identify and encode GAMT. The invention also provides expression vectors, host cells, antibodies, agonists, and antagonists. The invention also provides methods for treating or preventing disorders associated with expression of GAMT.

9 Claims, 7 Drawing Sheets

|     |                                  | |
| --- | -------------------------------- | --- |
| 1   | M V L C P V I G K L L H K R V V L A S A S P R R Q E I L S N | 2496002 |
| 1   | M — — — — — — — — — — — — — — — — — — — — — — — — — — — — — | 3053783 |
| 1   | M — — — — — — — — — — — — — — — — — — — — — — — — — — — — — | GI 607854 |
| 31  | A G L R F E V V P S K F K E K L D K A S F A T P Y G Y A M E | 2496002 |
| 2   | — — — — — — — — — — — — — — — — — — — — — — — — — — — — — — | 3053783 |
| 2   | — — — — — — — — — — — — — — — — — — — — — — — — — — — — — — | GI 607854 |
| 61  | T A K Q K A L E V A N R L Y Q K D L R A P D V V I G A D T I | 2496002 |
| 2   | — — — — — — — — — — — — — — — — — — — — — — — — — — — — — — | 3053783 |
| 2   | — — — — — — — — — — — — — — — — — — — — — — — — — — — — — — | GI 607854 |
| 91  | V T V G G L I L E K P V D K Q D A Y R M L S R L S G R E H S | 2496002 |
| 2   | — — — — — — — — — — — — — — — — — — — — — — — — — — — — — — | 3053783 |
| 2   | — — — — — — — — — — — — — — — — — — — — — — — — — — — — — — | GI 607854 |
| 121 | V F T G V A I V H C S S K D H Q L D T R V S E F Y E E T K V | 2496002 |
| 2   | — — — — — — — — — — — — — — — — — — — — — — — — — — — — — — | 3053783 |
| 2   | — — — — — — — — — — — — — — — — — — — — — — — — — — — — — — | GI 607854 |

FIGURE 1A

| | | | | |
|---|---|---|---|---|
| 151 | K F S E L S E E L L W E Y V V H S G E P M D K A G G Y G I Q A | 2496002 |
| 2 | – – – – – – – – – – – – – – – – – – – D K A G G Y G I Q A | 3053783 |
| 2 | – – – – – – – – – – – – – – – – – – – – – – – – – – – – – | GI 607854 |
| 181 | L G G M L V E S V H G D F L N V V G F P L N H F C K Q L V K | 2496002 |
| 12 | L G G M L V E S V H G D F L N V V G F P L N H F C K Q L V K | 3053783 |
| 2 | – – – – – – – – – – – – – – – – – – – – – – – – – – – – – | GI 607854 |
| 211 | L Y Y P P R P E D L R R S V K H D S I P A A D T F E D L S D | 2496002 |
| 42 | L Y Y P P R P E D L R R S V K H D S I P A A D T F E D L S D | 3053783 |
| 2 | – – – – – – – – – – – – – – – – – – – – – – – – – – – – – | GI 607854 |
| 241 | V E G G G S E P T Q R D A G S R D E K A E A G E A G Q A T A | 2496002 |
| 72 | V E G G G S E P T Q R D A G S R D E K A E A G E A G Q A T A | 3053783 |
| 2 | – – – – – G S S – E – – – – – – – – – – – – – – D Q A – | GI 607854 |
| 271 | E A E C H R T R E T L P P F P T R – L L E L I E G F M L S K | 2496002 |
| 102 | E A E C H R T R E T L P P F P T R – L L E L I E G F M L S K | 3053783 |
| 9 | – – – – – – – – – – – – – – – – – Y R L L N D Y A N G F M V S Q | GI 607854 |

331  S A C G M E R L L D I C A A M G L L E K T E Q G Y S N T E T  2496002
                    L L D I G A A M G                          MT Motifs
                       Motif I

```
421  SPETRLRFMRAMHSMTKLTACQVATAFNLS              2496002
451  RFSS ACDVGGCTGA LARELAREYPRMQVTV            2496002
          ACDVGGCLGA                             MT Motifs
          Motif III
481  FDLPDIIELAAHFQPPGPQAVQIHFAAGDF              2496002
511  FRDPLPSAELYVLCRILHDWPDDKVHKLLS              2496002
541  RVAESCKPGAGLLLVETLLDEEKRVAQRAL              2496002
571  MQSLNMLVQTEGKERSLGEYQCLLELHGFH              2496002
601  QVQVVHLGGVLDAILATKVAP                       2496002
```

FIGURE 2C

HUMAN GROWTH-ASSOCIATED METHYLTRANSFEASES

FIELD OF THE INVENTION

This invention relates to nucleic acid and amino acid sequences of two human growth-associated methyltransferases and to the use of these sequences in the diagnosis, treatment, and prevention of neoplastic, immunological, reproductive, developmental, and vesicle trafficking disorders.

BACKGROUND OF THE INVENTION

Covalent modification of cellular substrates with methyl groups has been implicated in the pathology of cancer and other diseases. (Gloria, L. et al. (1996) Cancer 78:2300–2306.) Cytosine hypermethylation of eukaryotic DNA prevents transcriptional activation. (Turker, M. S. and Bestor, T. H. (1997) Mutat. Res. 386:119–130.) $N^6$-methyladenosine is found at internal positions of mRNA in higher eukaryotes. (Bokar, J. A. et al. (1994) J. Biol. Chem. 269:17697–17704.) Hypermethylated viral DNA is transcribed at higher rates than hypo- or hemimethylated DNA in infected cells. (Willis, D. B. et al. (1989) Cell. Biophys. 15:97–111.)

Propagation of nerve impulses, modulation of cell proliferation and differentiation, induction of the immune response, and tissue homeostasis may involve neurotransmitter metabolism. (Weiss, B. (1991) Neurotoxicology 12:379–386; Collins, S. M. et al. (1992) Ann. N.Y. Acad. Sci. 664:415–424; and Brown, J. K. and Imam, H. (1991) J. Inherit. Metab. Dis. 14:436–458.) In tissue, synthesis and rates of degradation that regulate the activity of neurotransmitters are dependant upon enzyme and cofactor levels. (Brown, J. K. and Imam, H. supra.) Many pathways of small molecule degradation, such as those of neurotransmitters, require methyltransferase activity. (Kagan, R. M. and Clarke, S. (1994) Arch. Biochem. Biophys. 310:417–427.) For example, degradation of the catecholamines epinephrine or norepinephrine, requires catechol-O-methyltransferase, and N-acetyl-5-hydroxytryptamine is converted to melatonin by hydroxyindole-O-methyltransferase in the pineal gland. Both catechol-O-methyltransferase and hydroxyindole methyltransferase genes contain alternative initiation codons. (Rodriguez, I. R. et al. (1994) J. Biol. Chem. 269:31969–31977; and Tenhunen, J. et al. (1994) Eur. J. Biochem. 223:1049–1059.)

S-adenosylmethionine (AdoMet) is an important source of methyl groups for methylation reactions in the cell. (Bottiglieri, T. and Hyland, K. (1994) Acta Neurol. Scand. Suppl. 154:19–26.) Methyltransferase activity catalyzes the transfer of methyl groups from AdoMet to acceptor molecules such as phosphotidylethanolamine or the polynucleotide 5' cap of viral mRNA. (Montgomery, J. A. et al. (1982) J. Med. Chem. 25:626–629.)

Members of the protein and small molecule S-adenosylmethionine methyltransferase family (AdoMet-MT), utilize AdoMet as a substrate or product and harbor three common consensus sequence motifs. (Kagan and Clarke, supra.) Motifs I and II are characteristically spaced between 34 and 90 (mode 52, mean 57±13) amino acid residues apart; motifs II and III are spaced between 12 and 38 (mode 22, mean 22±5) residues apart. Motif I comprises part of the AdoMet binding pocket; motif II may also be involved in binding AdoMet; the role of motif III is uncertain. The main exceptions to the spacing rule are the RNA methyltransferases and a number of the porphyrin precursor methyltransferases. It has been suggested that these heterogeneic motifs may be of use in predicting methyltransferases and related enzymes from open reading frames generated genomic sequencing projects. (Kagan and Clarke, supra.)

Messenger RNA $N^6$-adenosine methyltransferase holoenzyme has been partially purified from HeLa cell nuclear extract to yield three subunits, an 875 kDa ssDNA-agarose binding protein, a 70 kDa AdoMet-binding protein, and an approximately 30 kDa component with unknown function. The three components are absolutely required for RNA $m^6$A-methylation activity. (Bokar, J. A., supra.)

In many tissues, including brain, gut, bone marrow, liver, and kidney, serine hydroxymethyltransferase converts serine to glycine by transferring the hydroxymethyl side chain group of serine to the methyl acceptor, tetrahydrofolate. The product of this reaction is $N^5$, $N^{10}$-methylenetetrahydrofolate and water. $N^5$, $N^{10}$-methylenetetrahydrofolate is a substrate in de novo purine nucleotide synthesis and pyrimidine nucleotide synthesis, in conversion of homocysteine to methionine, and in methylation of tRNA, during tissue growth and cell proliferation.

The genes encoding many of the growth-associated methyltransferases have not yet been identified or isolated. In their roles as a rate-limiting step in methyltransferase reactions, AdoMet-MTs have been identified as a target for psychiatric, antiviral, anticancer and anti-inflammatory drug design. (Bottiglieri, T. and Hyland, K., supra; Gloria, L. et al., supra.) Sequence-specific methylation inhibits the activity of the Epstein-Barr virus LMP1 and BCR2 enhancer-promoter regions. (Minarovits, J. et al. (1994) Virology 200:661–667.) 2'–5'-linked oligo (adenylic acid) nucleoside analogues synthesized by interferon-treated mouse L cells act as antiviral agents. (Goswami, B. B. et al, (1982) J. Biol. Chem. 257:6867–6870.) Adenine analogue inhibitors of AdoMet-MT decreased nucleic acid methylation and proliferation of leukemia L1210 cells. (Kramer, D. L. et al. (1990) Cancer Res. 50:3838–3842.)

The use of experimental neuroactive drugs has shown that inactivation of neurotransmitters is absolutely essential for the correct functioning of the nervous system. (Avery, L. and Horvitz, H. R. (1990) J. Ex. Zool. 253:263–270.) Epigenetic or genetic defects in neurotransmitter metabolic pathways can result in a spectrum of disease states in different tissues including Parkinson disease and inherited myoclonus. (McCance, K. L. and Huether, S. E. (1994) *Pathophysiology*, Mosby-Year Book, Inc., St. Louis, Mo. pp. 402–404; and Gundlach, A. L. (1990) FASEB J. 4:2761–2766.)

The discovery of two new human growth-associated methyltransferases and the polynucleotides encoding them satisfies a need in the art by providing new compositions which are useful in the diagnosis, treatment, and prevention of neoplastic, immunological, reproductive, developmental, and vesicle trafficking disorders.

SUMMARY OF THE INVENTION

The invention features substantially purified polypeptides, human growth-associated methyltransferases, referred to collectively as "GAMT" and individually as "GAMT-1" and "GAMT-2." In one aspect, the invention provides a substantially purified polypeptide comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant having at least 90% amino acid identity to the amino acid sequences of SEQ ID NO:1 or SEQ ID NO:3, or to a fragment of either of these sequences. The invention also provides an isolated and purified polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide having a sequence which is complementary to the polynucleotide encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% polynucleotide sequence identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide having a sequence which is complementary to the polynucleotide comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence selected from the group consisting of SEQ ID NO:1, SEQ ID NO:3, a fragment of SEQ ID NO:1, and a fragment of SEQ ID NO:3, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:3, a fragment of SEQ ID NO:1, and a fragment of SEQ ID NO:3 in conjunction with a suitable pharmaceutical carrier.

The invention further includes a purified antibody which binds to a polypeptide comprising the amino acid sequence selected from the group consisting of SEQ ID NO:1, SEQ ID NO:3, a fragment of SEQ ID NO:1, and a fragment of SEQ ID NO:3, as well as a purified agonist and a purified antagonist to the polypeptide.

The invention also provides a method for treating or preventing a neoplastic disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing an immunological disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a reproductive disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a developmental disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a vesicle trafficking disorder, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for detecting a polynucleotide encoding the polypeptide comprising the amino acid sequence selected from the group consisting of SEQ ID NO:1, SEQ ID NO:3, a fragment of SEQ ID NO:1, and a fragment of SEQ ID NO:3 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence alignments among GAMT-1 (2496002; SEQ ID NO:1), GAMT-2 (3053783; SEQ ID NO:3), and human hydroxyindole-O-methyltransferase (GI 607854; SEQ ID NO:5), produced using the multisequence alignment program of LASERGENE software (DNASTAR, Inc., Madison Wis.).

FIGS. 2A, 2B, and 2C show the amino acid sequence alignments between GAMT-1 (2496002; SEQ ID NO:1) and the methyltransferase family motifs (MT Motifs), Motif I and Motif III, produced using the multisequence alignment program of LASERGENE software (DNASTAR, Inc., Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"GAMT," as used herein, refers to the amino acid sequences of substantially purified GAMT obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to GAMT, increases or prolongs the duration of the effect of GAMT. Agonists may include proteins, nucleic acids, carbohydrates, or any other molecules which bind to and modulate the effect of GAMT.

An "allelic variant," as this term is used herein, is an alternative form of the gene encoding GAMT. Allelic variants may result from at least one mutation in the nucleic acid sequence and may result in altered mRNAs or in polypeptides whose structure or fumction may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding GAMT, as described herein, include those sequences with deletions, insertions, or substitutions of different nucleotides, resulting in a polynucleotide the same as GAMT or a polypeptide with at least one functional characteristic of GAMT. Included within this definition are polymorphisms which may or may not be readily detectable using a particular oligonucleotide probe of the polynucleotide encoding GAMT, and improper or unexpected hybridization to allelic variants, with a locus other than the normal chromosomal locus for the polynucleotide sequence encoding GAMT. The encoded protein may also be "altered," and may contain deletions, insertions, or substitutions of amino acid residues which produce a silent change and result in a functionally equivalent GAMT. Deliberate amino acid substitutions may be made on the basis of similarity in polarity, charge, solubility, hydrophobicity, hydrophilicity, and/or the amphipathic nature of the residues, as long as the biological or immunological activity of GAMT is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of GAMT which are preferably about 5 to about 15 amino acids in length, most preferably 14 amino acids, and which retain some biological activity or immunological activity of GAMT. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer a Laboratory Manual*, Cold Spring Harbor Press, Plainview, N.Y., pp.1–5.)

The term "antagonist," as it is used herein, refers to a molecule which, when bound to GAMT, decreases the amount or the duration of the effect of the biological or immunological activity of GAMT. Antagonists may include proteins, nucleic acids, carbohydrates, antibodies, or any other molecules which decrease the effect of GAMT.

As used herein, the term "antibody" refers to intact molecules as well as to fragments thereof, such as Fab, F(ab')$_2$, and Fv fragments, which are capable of binding the epitopic determinant. Antibodies that bind GAMT polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic GAMT, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding GAMT or fragments of GAMT may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding GAMT, by Northern analysis is indicative of the presence of nucleic acids encoding GAMT in a sample, and thereby correlates with expression of the transcript from the polynucleotide encoding GAMT.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological functions of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of GAMT. For example, modulation may cause an increase or a decrease in protein activity, binding characteristics, or any other biological, functional, or immunological properties of GAMT.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding GAMT, or fragments thereof, or GAMT itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature.

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of GAMT, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

THE INVENTION

The invention is based on the discovery of two new human growth-associated methyltransferases (GAMT), the polynucleotides encoding GAMT, and the use of these compositions for the diagnosis, treatment, or prevention of neoplastic, immunological, reproductive, developmental, and vesicle trafficking disorders.

Nucleic acids encoding the GAMT-1 of the present invention were first identified in Incyte Clone 2496002 from the pheochromocytoma cDNA library (ADRETUT05) using a computer search, e.g., BLAST, for amino acid sequence alignments. A consensus sequence, SEQ ID NO:2, was derived from the following overlapping and/or extended nucleic acid sequences: Incyte Clones 2496002 (ADRETUT05), 860691 (BRAITUT03), 2668446 (ESGTUT02), 1391951 (THYRNOT03), 1757229 (PITUNOT03), 2723781 (LUNGTUT10), 1665422 (BRSTNOT09), 1311430 (COLNFET02), and 1571369 (UTRSNOT05).

Nucleic acids encoding the GAMT-2 of the present invention were first identified in Incyte Clone 3053783 from the peripancreatic lymph node cDNA library (LNODNOT08) using a computer search, e.g., BLAST, for amino acid sequence alignments. A consensus sequence, SEQ ID NO:4, was derived from the following overlapping and/or extended nucleic acid sequences: Incyte Clones 3053783 (LNODNOT08), 2668446 (ESGTUT02), 1311430 (COLNFET02), 2457738 (ENDANOT01) and 486584 (HNT2RAT01).

In one embodiment, the invention encompasses a polypeptide comprising the amino acid sequence of SEQ ID NO:1. As shown in FIGS. 1A, 1B, 1C, and 1D, GAMT-1 is 621 amino acids in length and has a potential N-glycosylation site at N448; fourteen potential casein kinase II phosphorylation sites at residues S115, S131, T234, S239, T249, S255, S326, S356, S367, T389, S454, T479, T557, and S586; seven potential protein kinase C phosphorylation sites at residues S21, T61, S115, S131, S223, T249, and S545; and a potential signal peptide sequence from M1 through G22. As shown in FIGS. 2A, 2B, and 2C, GAMT-1 has two motifs, Motifs I and III, characteristic of the methyltransferase family. As shown in FIGS. 1A, 1B, 1C, and 1D, GAMT-1 has chemical and structural similarity with human hydroxyindole-O-methyltransferase (GI 607854; SEQ ID NO:5). In particular, GAMT-1 and human hydroxyindole-O-methyltransferase share 39% identity, two potential casein kinase II phosphorylation sites, one potential protein kinase C phosphorylation site, and the heterogeneic methyltransferase motifs, Motifs I and III. A fragment of SEQ ID NO:2 from about nucleotide 50 to about nucleotide 73 is useful, for example, for designing oligonucleotides or as a hybridization probe. Northern analysis shows the expression of this sequence in various libraries, at least 71% of which are immortalized or cancerous, 44% are in reproductive tissue, and at least 21% of which involve immune response. Of particular note is the expression of GAMT-1 in cancer, reproductive, fetal, inflanmmatory, and nervous tissues.

In one embodiment, the invention encompasses a polypeptide comprising the amino acid sequence of SEQ ID NO:3. GAMT-2 is 452 amino acids in length and has a potential N-glycosylation site at N279; twelve potential casein kinase II phosphorylation sites at residues T65, S70, T80, S86, S157, S187, S198, T220, S285, T310, T388, and S417; and three potential protein kinase C phosphorylation sites at residues S54, T80, and S376. As shown in FIGS. 1A, 1B, 1C, and 1D, GAMT-2 has chemical and structural homology with GAMT-1, and are considered to be splice variants. In addition, as shown in FIGS. 1A, 1B, 1C, and 1D, GAMT-2 has chemical and structural similarity with human hydroxyindole-O-methyltransferase (GI 607854; SEQ ID NO:5). In particular, GAMT-2 and human hydroxyindole-O-methyttransferase share 39% identity, two potential casein kinase II phosphorylation sites, one potential protein kinase C phosphorylation site, and the heterogeneic methyltransferase motifs, Motifs I and III. A fragment of SEQ ID NO:4 from about nucleotide 864 to about nucleotide 893 is useful, for example, for designing oligonucleotides or as a hybridization probe. Northern analysis shows the expression of this sequence in various libraries, at least 63% of which are immortalized or cancerous, 44% are in reproductive tissue, and at least 20% of which involve immune response. Of particular note is the expression of GAMT-2 in cancer, reproductive, fetal, inflammatory, and cardiovascular tissues.

The invention also encompasses GAMT variants. A preferred GAMT variant is one which has at least about 80%, more preferably at least about 90%, and most preferably at least about 95% amino acid sequence identity to the GAMT amino acid sequence, and which contains at least one functional or structural characteristic of GAMT.

The invention also encompasses polynucleotides which encode GAMT. In a particular embodiment, the invention encompasses a polynucleotide sequence comprising the sequence of SEQ ID NO:2 which encodes a GAMT. In a further embodiment, the invention encompasses the polynucleotide sequence comprising the sequence of SEQ ID NO:4 which encodes a GAMT.

The invention also encompasses a variant of a polynucleotide sequence encoding GAMT. In particular, such a variant polynucleotide sequence will have at least about 80%, more preferably at least about 90%, and most preferably at least about 95% polynucleotide sequence identity to the polynucleotide sequence encoding GAMT. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of GAMT.

It will be appreciated by those skilled in the art that as a result of the degeneracy of the genetic code, a multitude of polynucleotide sequences encoding GAMT, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring GAMT, and all such variations are to be considered as being specifically disclosed.

Although nucleotide sequences which encode GAMT and its variants are preferably capable of hybridizing to the nucleotide sequence of the naturally occurring GAMT under appropriately selected conditions of stringency, it may be advantageous to produce nucleotide sequences encoding GAMT or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GAMT and its derivatives without altering the encoded amino acid sequences include the production of RNA transcripts having more desirable properties, such as a greater half-life, than transcripts produced from the naturally occurring sequence.

The invention also encompasses production of DNA sequences which encode GAMT and GAMT derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding GAMT or any fragment thereof.

Also encompassed by the invention are polynucleotide sequences that are capable of hybridizing to the claimed polynucleotide sequences, and, in particular, to those shown in SEQ ID NO:2, SEQ ID NO:4, a fragment of SEQ ID NO:2, or a fragment of SEQ ID NO.4 under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the MICROLAB 2200 (Hamilton, Reno, Nev.), Peltier thermal cycler (PTC200; MJ Research, Watertown, Mass.) and the ABI CATALYST and 373 and 377 DNA SEQUENCERS (Perkin Elmer).

The nucleic acid sequences encoding GAMT may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO 4.06 primer analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode GAMT may be cloned in recombinant DNA molecules that direct expression of GAMT, or fragments or functional equivalents thereof, in appropriate host cells. Due to the inherent degeneracy of the genetic code, other DNA sequences which encode substantially the same or a functionally equivalent amino acid sequence may be produced and used to express GAMT.

The nucleotide sequences of the present invention can be engineered using methods generally known in the art in order to alter GAMT-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding GAMT may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, GAMT itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431 A peptide synthesizer (Perkin Elmer). Additionally, the amino acid sequence of GAMT, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active GAMT, the nucleotide sequences encoding GAMT or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding GAMT. Such elements may vary in their strength and specificity. Specific initiation signals may also be used to achieve more efficient translation of sequences encoding GAMT. Such signals include the ATG initiation codon and adjacent sequences, e.g. the Kozak sequence. In cases where sequences encoding GAMT and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding GAMT and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding GAMT. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding GAMT. For example, routine cloning, subcloning, and propagation of polynucleotide sequences encoding GAMT can be achieved using a multifunctional *E. coli* vector such as BLUESCRIPT (Stratagene) or PSPORT 1 plasmid (GIBCO/BRL). Ligation of sequences encoding GAMT into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of GAMT are needed, e.g. for the production of antibodies, vectors which direct high level expression of GAMT may be used. For example, vectors containing the strong, inducible T5 or T7 bacteriophage promoter may be used.

Yeast expression systems may be used for production of GAMT. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of GAMT. Transcription of sequences encoding GAMT may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology*(1992) McGraw Hill, New York, N.Y.; pp. 191–196.)

In mammalian cells, a number of viral-based expression systems may be utilized. In cases where an adenovirus is used as an expression vector, sequences encoding GAMT may be ligated into an adenovirus transcription/translation complex consisting of the late promoter and tripartite leader sequence. Insertion in a non-essential E1 or E3 region of the viral genome may be used to obtain infective virus which expresses GAMT in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of GAMT in cell lines is preferred. For example, sequences encoding GAMT can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate GUS, luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding GAMT is inserted within a marker gene sequence, transformed cells containing sequences encoding GAMT can be identified by the absence of marker gene function. Alternatively, a marker gene can be placed in tandem with a sequence encoding GAMT under the control of a single promoter. Expression of the marker gene in response to induction or selection usually indicates expression of the tandem gene as well.

In general, host cells that contain the nucleic acid sequence encoding GAMT and that express GAMT may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of GAMT using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on GAMT is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding GAMT include oligolabeling, nick translation, end-labeling, or PCR amplification using a labeled nucleotide. Alternatively, the sequences encoding GAMT, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding GAMT may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode GAMT may be designed to contain signal sequences which direct secretion of GAMT through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding GAMT may be ligated to a heterologous sequence resulting in translation of a fusion protein in any of the aforementioned host systems. For example, a chimeric GAMT protein containing a heterologous moiety that can be recognized by a commercially available antibody may facilitate the screening of peptide libraries for inhibitors of GAMT activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the GAMT encoding sequence and the heterologous protein sequence, so that GAMT may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled GAMT may be achieved in vitro using the TNT rabbit reticulocyte lysate or wheat germ extract systems (Promega, Madison, Wis). These systems couple transcription and translation of protein-coding sequences operably associated with the T7, T3, or SP6 promoters. Translation takes place in the presence of a radiolabeled amino acid precursor, preferably $^{35}$S-methionine.

Fragments of GAMT may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A peptide synthesizer (Perkin Elmer). Various fragments of GAMT may be synthesized separately and then combined to produce the full length molecule.

THERAPEUTICS

Chemical and structural similarity exists between GAMT-1 and human hydoxyindole-O-methyltransferase (GI 607854). In addition, GAMT-1 is expressed in cancer, reproductive, fetal, inflammatory, and nervous tissues. Therefore, GAMT-1 appears to play a role in neoplastic, immunological, reproductive, developmental, and vesicle trafficking disorders.

Chemical and structural similarity exists between GAMT-2 and human hydoxyindole-O-methyltransferase (GI 607854). In addition, GAMT-2 is expressed in cancer, reproductive, fetal, inflammatory, and cardiovascular tissues. Therefore, GAMT-2 appears to play a role in neoplastic, immunological, reproductive, developmental, and vesicle trafficking disorders.

Therefore, in one embodiment, an antagonist of GAMT may be administered to a subject to treat or prevent a neoplastic disorder. Such neoplastic disorders can include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds GAMT may be used directly as an antagonist or indirectly as a targeting or delivery mechanism for bringing a pharmaceutical agent to cells or tissue which express GAMT.

In an additional embodiment, a vector expressing the complement of the polynucleotide encoding GAMT may be administered to a subject to treat or prevent a neoplastic disorder including, but not limited to, those described above.

In one embodiment, an antagonist of GAMT may be administered to a subject to treat or prevent an immunological disorder. Such immunological disorders can include, but are not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, an antibody which specifically binds GAMT may be used directly as an antagonist or indirectly as a targeting or delivery mechanism for bringing a pharmaceutical agent to cells or tissue which express GAMT.

In an additional embodiment, a vector expressing the complement of the polynucleotide encoding GAMT may be administered to a subject to treat or prevent an immunological disorder including, but not limited to, those described above.

In one embodiment, an antagonist of GAMT may be administered to a subject to treat or prevent a reproductive disorder. Such reproductive disorders can include, but are not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis, carcinoma of the male breast and gynecomastia. In one aspect, an antibody which specifically binds GAMT may be used directly as an antagonist or indirectly as a targeting or delivery mechanism for bringing a pharmaceutical agent to cells or tissue which express GAMT.

In an additional embodiment, a vector expressing the complement of the polynucleotide encoding GAMT may be administered to a subject to treat or prevent a reproductive disorder including, but not limited to, those described above.

In one embodiment, a pharmaceutical composition comprising a substantially purified GAMT in conjunction with a suitable pharmaceutical carrier may be administered to a subject to treat or prevent a developmental disorder. The term "developmental disorder" refers to any disorder associated with growth and differentiation, embryogenesis, and morphogenesis involving any tissue, organ, or system of a subject (such as the brain, adrenal gland, kidney, skeletal or reproductive system). Such developmental disorders can include, but are not limited to, renal tubular acidosis, anemia, Cushing's syndrome, achondroplastic dwarfism, Duchenne and Becker muscular dystrophy, epilepsy, gonadal dysgenesis, WAGR syndrome, Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss.

In another embodiment, a vector capable of expressing GAMT or a fragment or derivative thereof may be administered to a subject to treat or prevent a developmental disorder including, but not limited to, those described above.

In a further embodiment, GAMT or a fragment or derivative thereof may be administered to a subject to treat or prevent a developmental disorder including, but not limited to, those provided above.

In still another embodiment, an agonist which modulates the activity of GAMT may be administered to a subject to treat or prevent a developmental disorder including, but not limited to, those listed above.

In one embodiment, a pharmaceutical composition comprising a substantially purified GAMT in conjunction with a suitable pharmaceutical carrier may be administered to a subject to treat or prevent a vesicle trafficking disorder. Such vesicle trafficking disorders can include, but are not limited to, cystic fibrosis, glucose-galactose malabsorption syndrome, hypercholesterolemia, diabetes mellitus, diabetes insipidus, hyper-and hypoglycemia, Grave's disease, goiter, Cushing's disease, and Addison's disease; gastrointestinal disorders including ulcerative colitis, gastric and duodenal ulcers; other conditions associated with abnormal vesicle trafficking including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections.

In another embodiment, a vector capable of expressing GAMT or a fragment or derivative thereof may be administered to a subject to treat or prevent a vesicle trafficking disorder including, but not limited to, those described above.

In a further embodiment, GAMT or a fragment or derivative thereof may be administered to a subject to treat or prevent a vesicle trafficking disorder including, but not limited to, those provided above.

In still another embodiment, an agonist which modulates the activity of GAMT may be administered to a subject to treat or prevent a vesicle trafficking disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of GAMT may be produced using methods which are generally known in the art. In particular, purified GAMT may be used to produce antibodies or to screen libraries of pharmaceutical agents to identify those which specifically bind GAMT. Antibodies to GAMT may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with GAMT or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to GAMT have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of GAMT amino acids may be fused with those of another protein, such as KLH, and antibodies to the chimeric molecule may be produced.

Monoclonal antibodies to GAMT may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce GAMT-specific single chain antibodies. Antibodies with related specificity, but of distinct idiotypic composition, may be generated by chain shuffling from random combinatorial irumunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for GAMT may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GAMT and its specific antibody. A two-site, monoclonal-based immunoassay utilizing monoclonal antibodies reactive to two non-interfering GAMT epitopes is preferred, but a competitive binding assay may also be employed. (Maddox, supra.)

In another embodiment of the invention, the polynucleotides encoding GAMT, or any fragment or complement thereof, may be used for therapeutic purposes. In one aspect, the complement of the polynucleotide encoding GAMT may be used in situations in which it would be desirable to block the transcription of the mRNA. In particular, cells may be transformed with sequences complementary to polynucleotides encoding GAMT. Thus, complementary molecules or fragments may be used to modulate GAMT activity, or to achieve regulation of gene function. Such technology is now well known in the art, and sense or antisense oligonucleotides or larger fragments can be designed from various locations along the coding or control regions of sequences encoding GAMT.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding GAMT. (See, e.g., Sambrook, supra; and Ausubel, supra.)

Genes encoding GAMT can be turned off by transforming a cell or tissue with expression vectors which express high levels of a polynucleotide, or fragment thereof, encoding GAMT. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding GAMT. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp.

163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding GAMT.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GAMT. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of GAMT, antibodies to GAMT, and mimetics, agonists, antagonists, or inhibitors of GAMT. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of GAMT, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example GAMT or fragments thereof, antibodies of GAMT, and agonists, antagonists or inhibitors of GAMT, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD50$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind GAMT may be used for the diagnosis of disorders characterized by expression of GAMT, or in assays to monitor patients being treated with GAMT or agonists, antagonists, or inhibitors of GAMT. Antibodies useful for diagnostic purposes may be prepared in the same manner as described above for therapeutics. Diagnostic assays for GAMT include methods which utilize the antibody and a label to detect GAMT in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring GAMT, including ELISAs, RIAs, and FACS, are known in the art and provide a basis for diagnosing altered or abnormal levels of GAMT expression. Normal or standard values for GAMT expression are established by combining body fluids or cell extracts taken from normal mammalian subjects, preferably human, with antibody to GAMT under conditions suitable for complex formation. The amount of standard complex formation may be quantitated by various methods, preferably by photometric means. Quantities of GAMT expressed in subject samples from biopsied tissues are compared with the standard values. Deviation between standard and subject values establishes the parameters for diagnosing disease.

In another embodiment of the invention, the polynucleotides encoding GAMT may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of GAMT may be correlated with disease. The diagnostic assay may be used to determine absence, presence, and excess expression of GAMT, and to monitor regulation of GAMT levels during therapeutic intervention.

In one aspect, hybridization with PCR probes which are capable of detecting polynucleotide sequences, including genomic sequences, encoding GAMT or closely related molecules may be used to identify nucleic acid sequences which encode GAMT. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding GAMT, allelic variants, or related sequences.

Probes may also be used for the detection of related sequences, and should preferably have at least 50% sequence identity to any of the GAMT encoding sequences. The hybridization probes of the subject invention may be DNA or RNA and may be derived from the sequence of SEQ ID NO:2, SEQ ID NO:4, or from genomic sequences including promoters, enhancers, and introns of the GAMT gene.

Means for producing specific hybridization probes for DNAs encoding GAMT include the cloning of polynucleotide sequences encoding GAMT or GAMT derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding GAMT may be used for the diagnosis of a disorder associated with expression of GAMT. Examples of such a disorder include, but are not limited to, a neoplastic disorder, such as, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an immunological disorder, such as, AIDS, Addison's disease, adult respiratory distress syndrome, allergies, ankylosing spondylitis, amyloidosis, anemia, asthma, atherosclerosis, autoinumune hemolytic anemia, autoimmune thyroiditis, bronchitis, cholecystitis, contact dermatitis, Crohm's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma; a reproductive disorder such as, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, and prostatitis, carcinoma of the male breast and gynecomastia; a developmental disorder, such as, renal tubular acidosis, anemia, Cushing's syndrome, achondroplastic dwarfism, Duchenne and Becker muscular dystrophy, epilepsy, gonadal dysgenesis, WAGR syndrome, Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, congenital glaucoma, cataract, and sensorineural hearing loss; and a vesicle trafficking disorder, such as, cystic fibrosis, glucose-galactose malabsorption syndrome, hypercholesterolemia, diabetes mellitus, diabetes insipidus, hyper-and hypoglycemia, Grave's disease, goiter, Cushing's disease, and Addison's disease; gastrointestinal disorders including ulcerative colitis, gastric and duodenal ulcers; other conditions associated with abnormal vesicle trafficking including AIDS; allergies including hay fever, asthma, and urticaria (hives); autoimmune hemolytic anemia; proliferative glomerulonephritis; inflammatory bowel disease; multiple sclerosis; myasthenia gravis; rheumatoid and osteoarthritis; scleroderma; Chediak-Higashi and Sjogren's syndromes; systemic lupus erythematosus; toxic shock syndrome; traumatic tissue damage; and viral, bacterial, fungal, helminth, and protozoal infections. The polynucleotide sequences encoding GAMT may be used in Southern or Northern analysis, dot blot, or other membrane-based technologies; in PCR technologies; in dipstick, pin, and ELISA assays; and in microarrays utilizing fluids or tissues from patients to detect altered GAMT expression. Such qualitative or quantitative methods are well known in the art.

In a particular aspect, the nucleotide sequences encoding GAMT may be useful in assays that detect the presence of associated disorders, particularly those mentioned above. The nucleotide sequences encoding GAMT may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding GAMT in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of GAMT, a normal or standard profile for expression is established. This may be accomplished by combining body fluids or cell extracts taken from normal subjects, either animal or human, with a sequence, or a fragment thereof, encoding GAMT, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GAMT may involve the use of PCR. These oligomers may be chemically synthesized, generated enzymatically, or produced in vitro. Oligomers will preferably contain a fragment of a polynucleotide encoding GAMT, or a fragment of a polynucleotide complementary to the polynucleotide encoding GAMT, and will be employed under optimized conditions for identification of a specific gene or condition. Oligomers may also be employed under less stringent conditions for detection or quantitation of closely related DNA or RNA sequences.

Methods which may also be used to quantitate the expression of GAMT include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding GAMT may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding GAMT on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, GAMT, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between GAMT and the agent being tested may be measured.

Another technique for drug screening provides for high throughput screening of compounds having suitable binding affinity to the protein of interest. (See, e.g., Geysen, et al. (1984) PCT application WO84103564.) In this method, large numbers of different small test compounds are synthesized on a solid substrate, such as plastic pins or some other surface. The test compounds are reacted with GAMT, or fragments thereof, and washed. Bound GAMT is then detected by methods well known in the art. Purified GAMT can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GAMT specifically compete with a test compound for binding GAMT. In this manner, antibodies can be used to detect the presence of any peptide which shares one or more antigenic determinants with GAMT.

In additional embodiments, the nucleotide sequences which encode GAMT may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

ADRETUT05

The ADRETUT05 cDNA library was constructed from tumor tissue obtained from the right adrenal gland of a 52 year-old Caucasian female (specimen #0058) during a unilateral adrenalectomy. Pathology indicated a pheochromocytoma. Patient history included benign hypertension, depressive disorder, chronic sinusitis, idiopathic proctocolitis, urinary tract infection, and irritable colon. Patient medications included PROCARDIA (one dose only) (Pratt Pharmaceuticals Division of Pfizer Inc., New York, N.Y.) and PROZAC for 5 years (floroxetine hydrochloride; Dista Products and Eli Lilly and Company, Indianapolis, Ind.). Family history included benign hypertension in a sibling; cerebrovascular disease, secondary Parkinsonism, and irritable colon in the mother; atherosclerotic coronary artery disease, hyperlipidemia, and malignant brain neoplasm in siblings; and secondary Parkinsonism in the father.

LNODNOT08

The LNODNOT08 cDNA library was constructed from peripancreatic lymph node tissue removed from a 65-year-old Caucasian male during radical pancreaticoduodenectomy and cholecystectomy. Pathology indicated a reactive lymph node. Pathology for the associated tumor tissue indicated infiltrating grade 3 adenocarcinoma, ductal type. Multiple (2 of 5) peripancreatic lymph nodes contained metastatic adenocarcinoma. Patient family history included acute myocardial infarction and atherosclerotic coronary artery disease in the mother; acute myocardial infarction, angina pectoris, and atherosclerotic coronary disease in the father, and colon cancer in the grandparents.

For both libraries, the frozen tissue was homogenized and lysed in guanidinium isothiocyanate solution using a Polytron PT-3000 homogenizer (Brinkmann Instruments, Westbury, N.Y.). The lysate was centrifuged over a CsCI cushion to isolate RNA. Alternatively, RNA was isolated using TRIzol reagent (Catalog #10296–028, GIBCO-BRL, Gaithersburg, Md.), a monophasic solution of phenol and guanidine isothiocyanate. The RNA was extracted with acid phenol, precipitated with sodium acetate and ethanol, resuspended in RNase-free water, and treated with DNase. The RNA was extracted and precipitated as before. Poly(A+) RNA was isolated using the OLIGOTEX kit (QIAGEN Inc, Chatsworth, Calif.). This procedure may have been modified to accommodate the specific kits, plasmids, reagents, and machinery available at the time of each library's construction.

Poly(A+) RNA was used for cDNA synthesis and construction of the cDNA libraries according to the recommended protocols in the SUPERSCRIPT plasmid system (Catalog #18248-013, GIBCO-BRL). cDNA synthesis was initiated with a NotI-oligo d(T) primer. Double stranded cDNA was blunted, ligated to EcoRI adaptors, digested with NotI, fractionated on a SEPHAROSE CL4B column (Catalog #275105-01, Pharmacia, Piscataway, N.J.), and those cDNAs exceeding 400 bp were ligated into the NotI and EcoRI sites of the cloning vector, pINCY 1 (Incyte). The recombinant plasmids were subsequently transformed into DH5α competent cells (Catalog #18258-012, GIBCO-BRL).

II. Isolation and Sequencing of cDNA Clones

Plasmid DNA was released from the cells and purified using the R.E.A.L PREP 96 plasmid kit (Catalog #26173, QIAGEN Inc). The recommended protocol was employed except for the following changes: 1) the bacteria were cultured in 1 ml of sterile Terrific Broth (Catalog #22711, GIBCO-BRL) with carbenicillin at 25 mg/l and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4° C.

The cDNAs were sequenced by the method of Sanger et al. (1975, J. Mol. Biol. 94:441f), using a MICROLAB 2200 (Hamilton, Reno, Nev.) in combination with Peltier thermal cyclers (PTC200 from MJ Research, Watertown, Mass.) and Applied Biosystems 377 DNA sequencing systems, and the reading frame was determined.

III. Similarity Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. and Henikoff G. J., Nucleic Acids Research (1991) 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding GAMT occurs. Abundance and percent abundance are also reported. Abundance directly reflects the number of times a particular transcript is represented in a cDNA library, and percent abundance is abundance divided by the total number of sequences examined in the cDNA library.

V. Extension of GAMT Encoding Polynucleotides

The nucleic acid sequences of Incyte Clones 2496002 and 3053783 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 μl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2, SEQ ID NO:4, are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2, SEQ ID NO:4, are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham, Chicago, Ill.), and T4 polynucleotide kinase (DuPont NEN, Boston, Mass.). The labeled oligonucleotides are substantially purified using a SEPHADEX G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN, Boston, Mass.).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the GAMT-encoding sequences, or any parts thereof, are used to detect, decrease, or inhibit expression of naturally occurring GAMT. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of GAMT. To inhibit transcription, a complementary oligonucleotide is designed from the most unique 5' sequence and used to prevent promoter binding to the coding sequence. To inhibit translation, a complementary oligonucleotide is designed to prevent ribosomal binding to the GAMT-encoding transcript.

IX. Expression of GAMT

Expression and purification of GAMT is achieved using bacterial or virus-based expression systems. For expression of GAMT in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express GAMT upon induction with isopropyl beta-D-thiogalactopyranoside (IPTG). Expression of GAMT in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding GAMT by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, GAMT is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from GAMT at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified GAMT obtained by these methods can be used directly in the following activity assay.

X Demonstration of GAMT Activity

A method that measures transfer of radiolabeled methyl groups between a donor substrate and an acceptor substrate is used to determine GAMT activity (Bokar, J. A. et al. supra). Reaction mixtures (50 μl final volume) contain 15 mM HEPES, pH 7.9, 1.5 mM $MgCl_2$, 10 mM dithiothreitol, 3% polyvinylalcohol, 1.5 μCi [methyl-$^3$H]AdoMet (0.375 μM AdoMet) (DuPont-NEN), 0.6 μg GAMT, and acceptor substrate (0.4 μg [$^{35}$S]RNA or 6-mercaptopurine (6-MP) to 1 mM final concentration). Reaction mixtures are incubated at 30° C. for 30 minutes, then 65° C. for 5 minutes.

Analysis of the product [methyl-$^3$H]RNA is as follows: 1) 50 μl of 2× loading buffer (20 mM tris-HCl, pH 7.6, 1 M LiCl, 1 mM EDTA, 1% sodium dodecyl sulphate (SDS)) and 50 μl oligo d(T)-cellulose (10 mg/ml in 1×loading buffer) are added to the reaction mixture, and incubated at ambient temperature with shaking for 30 minutes. 2) Reaction mixtures are transferred to a 96-well filtration plate attached to a vacuum apparatus. 3) Each sample is washed sequentially with three 2.4 ml aliquots of 1× oligo d(T) loading buffer containing 0.5% SDS, 0.1% SDS, or no SDS. 4) RNA is eluted with 300 μl of water into a 96-well collection plate, transferred to scintillation vials containing liquid scintillant, and radioactivity determined. The amount of radioactivity is proportional to the activity of GAMT.

Analysis of the product [methyl-$^3$H]6-MP is as follows: 1) 500 μl 0.5 M borate buffer, pH 10.0, and then 2.5 ml of 20% (v/v) isoamyl alcohol in toluene are added to the reaction mixtures. 2) The samples mixed by vigorous vortexing for ten seconds. 3) After centrifugation at 700 g for 10 minutes, 1.5 ml of the organic phase is transferred to scintillation vials containing 0.5 ml absolute ethanol and liquid scintillant, and radioactivity determined. 4) Results are corrected for the extraction of 6-MP into the organic phase (approximately 41%). The amount of radioactivity is proportional to the activity of GAMT.

XI. Functional Assays

GAMT function is assessed by expressing the sequences encoding GAMT at physiologically elevated levels in mammalian cell culture systems. cDNA is subcloned into a mammalian expression vector containing a strong promoter that drives high levels of cDNA expression. Vectors of choice include PCMV.SPORT1 (LIFE TECHNOLOGIES, Gaithersburg, Md.) and PCR 3.1 (INVITROGEN, Carlsbad, Calif., both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP and to evaluate properties such as their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of GAMT on gene expression can be assessed using highly purified populations of cells transfected with sequences encoding GAMT and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding GAMT and other genes of interest can be analyzed by Northern analysis or microarray techniques.

XII. Production of GAMT Specific Antibodies

GAMT substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the GAMT amino acid sequence is analyzed using LASERGENE software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XIII. Purification of Naturally Occurring GAMT Using Specific Antibodies

Naturally occurring or recombinant GAMT is substantially purified by immunoaffinity chromatography using antibodies specific for GAMT. An immunoaffinity column is constructed by covalently coupling anti-GAMT antibody to an activated chromatographic resin, such as CNBr-activated SEPHAROSE (Pharmacia & Upjohn). After the coupling, the resin is blocked and washed according to the manufacturer's instructions.

Media containing GAMT are passed over the immunoaffinity column, and the column is washed under conditions that allow the preferential absorbance of GAMT (e.g., high ionic strength buffers in the presence of detergent). The column is eluted under conditions that disrupt antibody/GAMT binding (e.g., a buffer of pH 2 to pH 3, or a high concentration of a chaotrope, such as urea or thiocyanate ion), and GAMT is collected.

XIV. Identification of Molecules Which Interact with GAMT

GAMT, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled GAMT, washed, and any wells with labeled GAMT complex are assayed. Data obtained using different concentrations of GAMT are used to calculate values for the number, affinity, and association of GAMT with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide encoding the polypeptide comprising an amino acid sequence selected from the group consisting of SEQ ID NO:1 and SEQ ID NO:3.

2. An isolated and purified polynucleotide having a sequence which is fully complementary to the polynucleotide sequence of claim 1.

3. An isolated and purified polynucleotide comprising a polynucleotide sequence selected from the group consisting of SEQ ID NO:2 and SEQ ID NO:4.

4. An isolated and purified polynucleotide having a sequence which is fully complementary to the polynucleotide of claim 3.

5. An expression vector comprising the polynucleotide of claim 1.

6. A host cell comprising the expression vector of claim 5.

7. A method for producing a polypeptide comprising the amino acid sequence selected from the group consisting of SEQ ID NO:1, and SEQ ID NO:3, the method comprising the steps of:
   a) culturing the host cell of claim 6 under conditions suitable for the expression of the polypeptide; and
   b) recovering the polypeptide from the host cell culture.

8. A method for detecting a polynucleotide encoding a growth-associated methyltransferase having an amino acid sequence selected from the group consisting of SEQ ID NO:1 and SEQ ID NO:3 in a biological sample, the method comprising the steps of:
   (a) hybridizing the polynucleotide of claim 2 to at least one of the nucleic acids in the biological sample, thereby forming a hybridization complex;
   (b) washing said hybridization complex at room temperature under increasingly stringent conditions up to 0.1× saline sodium citrate and 0.5% sodium dodecyl sulfate; and
   (c) detecting the hybridization complex, wherein the presence of the hybridization complex correlates with the presence of the polynucleotide encoding the polypeptide in the biological sample.

9. The method of claim 8 wherein the nucleic acids of the biological sample are amplified by the polymerase chain reaction prior to hybridization.

* * * * *

UNITED STATES PATENT AND TRADEMARK OFFICE
CERTIFICATE OF CORRECTION

PATENT NO. : 6,001,607

DATED : December 14, 1999

INVENTOR(S) : Y. Tom Tang, et al.

It is certified that error appears in the above-identified patent and that said Letters Patent is hereby corrected as shown below:

Title page, delete "[54] HUMAN GROWTH-ASSOCIATED METHYLTRANSFEASES" and insert --HUMAN GROWTH-ASSOCIATED METHYLTRANSFERASES--

Signed and Sealed this

Twenty-seventh Day of March, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 621 amino acids
      (B) TYPE: amino acid
      (C) STRANDEDNESS: single
      (D) TOPOLOGY: linear (vii) IMMEDIATE SOURCE:
      (A) LIBRARY: ADRETUT05
      (B) CLONE: 2496002

(xi) SEQUENCE DESCRIPTION: SEQ ID NO: 1 :

```
Met Val Leu Cys Pro Val Ile Gly Lys Leu Leu His Lys Arg Val
              5                  10                      15

Val Leu Ala Ser Ala Ser Pro Arg Arg Gln Glu Ile Leu Ser Asn
             20                  25                      30

Ala Gly Leu Arg Phe Glu Val Val Pro Ser Lys Phe Lys Glu Lys
             35                  40                      45

Leu Asp Lys Ala Ser Phe Ala Thr Pro Tyr Gly Tyr Ala Met Glu
             50                  55                      60

Thr Ala Lys Gln Lys Ala Leu Glu Val Ala Asn Arg Leu Tyr Gln
             65                  70                      75

Lys Asp Leu Arg Ala Pro Asp Val Val Ile Gly Ala Asp Thr Ile
```

```
                  80                  85                  90
Val Thr Val Gly Gly Leu Ile Leu Glu Lys Pro Val Asp Lys Gln
                      95                 100                 105
Asp Ala Tyr Arg Met Leu Ser Arg Leu Ser Gly Arg Glu His Ser
                     110                 115                 120
Val Phe Thr Gly Val Ala Ile Val His Cys Ser Ser Lys Asp His
                     125                 130                 135
Gln Leu Asp Thr Arg Val Ser Glu Phe Tyr Glu Thr Lys Val
                     140                 145                 150
Lys Phe Ser Glu Leu Ser Glu Glu Leu Leu Trp Glu Tyr Val His
                     155                 160                 165
Ser Gly Glu Pro Met Asp Lys Ala Gly Tyr Gly Ile Gln Ala
                     170                 175                 180
Leu Gly Gly Met Leu Val Glu Ser Val His Gly Asp Phe Leu Asn
                     185                 190                 195
Val Val Gly Phe Pro Leu Asn His Phe Cys Lys Gln Leu Val Lys
                     200                 205                 210
Leu Tyr Tyr Pro Pro Arg Pro Glu Asp Leu Arg Arg Ser Val Lys
                     215                 220                 225
His Asp Ser Ile Pro Ala Ala Asp Thr Phe Glu Asp Leu Ser Asp
                     230                 235                 240
Val Glu Gly Gly Gly Ser Glu Pro Thr Gln Arg Asp Ala Gly Ser
                     245                 250                 255
Arg Asp Glu Lys Ala Glu Ala Gly Glu Ala Gly Gln Ala Thr Ala
                     260                 265                 270
Glu Ala Glu Cys His Arg Thr Arg Glu Thr Leu Pro Pro Phe Pro
                     275                 280                 285
Thr Arg Leu Leu Glu Leu Ile Glu Gly Phe Met Leu Ser Lys Gly
                     290                 295                 300
Leu Leu Thr Ala Cys Lys Leu Lys Val Phe Asp Leu Leu Lys Asp
                     305                 310                 315
Glu Ala Pro Gln Lys Ala Ala Asp Ile Ala Ser Lys Val Asp Ala
                     320                 325                 330
Ser Ala Cys Gly Met Glu Arg Leu Leu Asp Ile Cys Ala Ala Met
                     335                 340                 345
Gly Leu Leu Glu Lys Thr Glu Gln Gly Tyr Ser Asn Thr Glu Thr
                     350                 355                 360
Ala Asn Val His Leu Ala Ser Asp Gly Glu Tyr Ser Leu His Gly
                     365                 370                 375
Phe Ile Met His Asn Asn Asp Leu Thr Trp Asn Leu Phe Thr Tyr
                     380                 385                 390
Leu Glu Phe Ala Ile Arg Glu Gly Thr Asn Gln His His Arg Ala
                     395                 400                 405
Leu Gly Lys Lys Ala Glu Asp Leu Phe Gln Asp Ala Tyr Tyr Gln
                     410                 415                 420
Ser Pro Glu Thr Arg Leu Arg Phe Met Arg Ala Met His Ser Met
                     425                 430                 435
Thr Lys Leu Thr Ala Cys Gln Val Ala Thr Ala Phe Asn Leu Ser
                     440                 445                 450
Arg Phe Ser Ser Ala Cys Asp Val Gly Gly Cys Thr Gly Ala Leu
                     455                 460                 465
Ala Arg Glu Leu Ala Arg Glu Tyr Pro Arg Met Gln Val Thr Val
                     470                 475                 480
```

-continued

```
Phe Asp Leu Pro Asp Ile Ile Glu Leu Ala Ala His Phe Gln Pro
            485                 490                 495

Pro Gly Pro Gln Ala Val Gln Ile His Phe Ala Ala Gly Asp Phe
            500                 505                 510

Phe Arg Asp Pro Leu Pro Ser Ala Glu Leu Tyr Val Leu Cys Arg
            515                 520                 525

Ile Leu His Asp Trp Pro Asp Asp Lys Val His Lys Leu Leu Ser
            530                 535                 540

Arg Val Ala Glu Ser Cys Lys Pro Gly Ala Gly Leu Leu Leu Val
            545                 550                 555

Glu Thr Leu Leu Asp Glu Glu Lys Arg Val Ala Gln Arg Ala Leu
            560                 565                 570

Met Gln Ser Leu Asn Met Leu Val Gln Thr Glu Gly Lys Glu Arg
            575                 580                 585

Ser Leu Gly Glu Tyr Gln Cys Leu Leu Glu Leu His Gly Phe His
            590                 595                 600

Gln Val Gln Val Val His Leu Gly Gly Val Leu Asp Ala Ile Leu
            605                 610                 615

Ala Thr Lys Val Ala Pro
            620
```

(2) INFORMATION FOR SEQ ID NO: 2:

(i) SEQUENCE CHARACTERISTICS:
        (A) LENGTH: 2057 base pairs
        (B) TYPE: nucleic acid
        (C) STRANDEDNESS: single
        (D) TOPOLOGY: linear (vii) IMMEDIATE SOURCE:
        (A) LIBRARY: ADRETUT05
        (B) CLONE: 2496002

(xi) SEQUENCE DESCRIPTION: SEQ ID NO: 2 :

```
GAAGTGCGGA CGCCCGGCTC CCGGCGTGGA CGCCATGGTG CTGTGCCCGG TGATTGGGAA      60

GCTGCTGCAC AAGCGCGTGG TGCTGGCCAG CGCCTCCCCA CGCCGTCAGG AGATCCTCAG     120

CAACGCGGGT CTCAGGTTTG AGGTGGTCCC CTCCAAGTTT AAAGAGAAGC TGGACAAAGC     180

CTCCTTCGCT ACTCCGTATG GGTACGCCAT GGAGACCGCC AAGCAGAAGG CCCTGGAGGT     240

GGCCAACCGG CTGTACCAGA AAGACCTGCG GGCCCCCGAC GTGGTCATTG AGCGGACAC      300

GATCGTGACG GTCGGGGGGC TGATTCTGGA AAGCCGGTG GACAAGCAGG ACGCCTACAG      360

GATGCTGTCC CGGTTGAGTG GGAGAGAACA CAGCGTGTTC ACAGGTGTCG CGATCGTCCA     420

CTGCTCCAGC AAAGACCATC AGCTGGACAC CAGGGTCTCG GAATTCTACG AGGAAACGAA     480

GGTGAAGTTC TCGGAGCTGT CCGAGGAGCT GCTCTGGGAA TACGTCCACA GCGGGGAGCC     540

CATGGACAAA GCTGGCGGCT ACGGGATCCA GGCCCTGGGC GGCATGCTGG TGGAGTCCGT     600

ACACGGGGAC TTTCTGAACG TGGTGGGATT CCCGCTGAAC CACTTCTGCA AGCAGCTGGT     660

GAAGCTCTAC TACCCGCCCC GTCCGGAGGA CCTGCGGCGG AGTGTCAAGC ACGACTCCAT     720

CCCGGCCGCG GACACCTTCG AAGACCTCAG TGACGTGGAG GGGGGTGGCT CGGAGCCCAC     780

TCAGGGGAC GCGGGCAGCC GCGATGAGAA GGCCGAGGCG GGAGAGGCGG ACAGGCCAC       840

GGCAGAGGCT GAGTGTCACA GGACTCGGGA GACCCTGCCT CCGTTCCCGA CACGCCTCCT    900

GGAGCTGATT GAGGGCTTTA TGCTATCCAA GGGCCTGCTC ACCGCTTGCA AACTGAAGGT    960

GTTCGATTTG TTAAAAGATG AAGCACCCCA GAAGGCTGCG GATATTGCCA GCAAAGTGGA   1020

CGCCTCTGCG TGTGGAATGG AGAGGCTTCT GGACATCTGT GCTGCCATGG GGCTCCTGGA   1080
```

-continued

```
GAAGACAGAG CAAGGTTACA GTAACACAGA GACAGCGAAC GTCCACCTGG CATCGGATGG    1140

CGAATACTCT CTGCACGGCT TCATCATGCA CAATAATGAC CTCACATGGA ACCTCTTTAC    1200

ATACCTGGAG TTTGCCATCC GAGAGGGAAC AAACCAGCAC CACAGGGCGT TGGGGAAGAA    1260

GGCGGAAGAT CTGTTCCAGG ATGCGTACTA CCAGAGCCCG GAGACGCGGC TGAGGTTCAT    1320

GCGGGCCATG CACAGCATGA CGAAGCTGAC TGCGTGCCAG GTGGCCACGG CCTTCAATCT    1380

GTCCCGCTTC TCCTCCGCCT GCGACGTGGG AGGCTGCACC GGTGCACTGG CCCGAGAGCT    1440

GGCCCGTGAG TACCCTCGTA TGCAGGTGAC TGTGTTTGAC CTCCCAGACA TTATCGAGCT    1500

GGCCGCCCAC TTCCAACCCC CCGGACCGCA GGCAGTGCAG ATCCACTTCG CAGCAGGTGA    1560

CTTTTTCAGG GACCCCCTCC CCAGCGCTGA GCTGTACGTC CTGTGCCGGA TCCTGCATGA    1620

CTGGCCAGAC GACAAAGTCC ACAAGTTACT CAGCAGGGTC GCCGAGAGCT GCAAGCCAGG    1680

GGCCGGCCTG CTGCTGGTGG AGACGCTCCT GGATGAGGAG AAGAGGGTGG CGCAGCGCGC    1740

CCTGATGCAG TCACTGAACA TGCTGGTGCA GACTGAAGGC AAGGAGCGGA GCCTGGGCGA    1800

GTATCAGTGC TTGCTGGAGC TGCACGGCTT CCACCAGGTG CAGGTGGTGC ACTTGGGGGG    1860

TGTCCTGGAT GCCATCTTGG CCACCAAAGT GGCCCCCTGA AGCCCAGGCA GCATGTTCAT    1920

TATAGGGATG TCCTCCCCCA GGCTGCAGGT GGACCGCCCG GTCCCAAGT ACCATAGGAC     1980

AGTCACATAG GAGCGTGTAG TCGTGACTGA ATAAAGAAAG CAAAAGCCAA AAAAAAAAA     2040

AAAGGGCGCT CGAGCCG                                                  2057
```

(2) INFORMATION FOR SEQ ID NO: 3:

(i) SEQUENCE CHARACTERISTICS:
        (A) LENGTH: 452 amino acids
        (B) TYPE: amino acid
        (C) STRANDEDNESS: single
        (D) TOPOLOGY: linear (vii) IMMEDIATE SOURCE:
        (A) LIBRARY: LNODNOT08
        (B) CLONE: 3053783

(xi) SEQUENCE DESCRIPTION: SEQ ID NO: 3 :

```
Met Asp Lys Ala Gly Gly Tyr Gly Ile Gln Ala Leu Gly Gly Met
                 5                  10                  15

Leu Val Glu Ser Val His Gly Asp Phe Leu Asn Val Val Gly Phe
                20                  25                  30

Pro Leu Asn His Phe Cys Lys Gln Leu Val Lys Leu Tyr Tyr Pro
                35                  40                  45

Pro Arg Pro Glu Asp Leu Arg Arg Ser Val Lys His Asp Ser Ile
                50                  55                  60

Pro Ala Ala Asp Thr Phe Glu Asp Leu Ser Asp Val Glu Gly Gly
                65                  70                  75

Gly Ser Glu Pro Thr Gln Arg Asp Ala Gly Ser Arg Asp Glu Lys
                80                  85                  90

Ala Glu Ala Gly Glu Ala Gly Gln Ala Thr Ala Glu Ala Glu Cys
                95                 100                 105

His Arg Thr Arg Glu Thr Leu Pro Pro Phe Pro Thr Arg Leu Leu
               110                 115                 120

Glu Leu Ile Glu Gly Phe Met Leu Ser Lys Gly Leu Leu Thr Ala
               125                 130                 135

Cys Lys Leu Lys Val Phe Asp Leu Leu Lys Asp Glu Ala Pro Gln
               140                 145                 150
```

```
Lys Ala Ala Asp Ile Ala Ser Lys Val Asp Ala Ser Ala Cys Gly
            155                 160                 165
Met Glu Arg Leu Leu Asp Ile Cys Ala Ala Met Gly Leu Leu Glu
            170                 175                 180
Lys Thr Glu Gln Gly Tyr Ser Asn Thr Glu Thr Ala Asn Val His
            185                 190                 195
Leu Ala Ser Asp Gly Glu Tyr Ser Leu His Gly Phe Ile Met His
            200                 205                 210
Asn Asn Asp Leu Thr Trp Asn Leu Phe Thr Tyr Leu Glu Phe Ala
            215                 220                 225
Ile Arg Glu Gly Thr Asn Gln His His Arg Ala Leu Gly Lys Lys
            230                 235                 240
Ala Glu Asp Leu Phe Gln Asp Ala Tyr Tyr Gln Ser Pro Glu Thr
            245                 250                 255
Arg Leu Arg Phe Met Arg Ala Met His Gly Met Thr Lys Leu Thr
            260                 265                 270
Ala Cys Gln Val Ala Thr Ala Phe Asn Leu Ser Arg Phe Ser Ser
            275                 280                 285
Ala Cys Asp Val Gly Gly Cys Thr Gly Ala Leu Ala Arg Glu Leu
            290                 295                 300
Ala Arg Glu Tyr Pro Arg Met Gln Val Thr Val Phe Asp Leu Pro
            305                 310                 315
Asp Ile Ile Glu Leu Ala Ala His Phe Gln Pro Pro Gly Pro Gln
            320                 325                 330
Ala Val Gln Ile His Phe Ala Ala Gly Asp Phe Phe Arg Asp Pro
            335                 340                 345
Leu Pro Ser Ala Glu Leu Tyr Val Leu Cys Arg Ile Leu His Asp
            350                 355                 360
Trp Pro Asp Asp Lys Val His Lys Leu Leu Ser Arg Val Ala Glu
            365                 370                 375
Ser Cys Lys Pro Gly Ala Gly Leu Leu Leu Val Glu Thr Leu Leu
            380                 385                 390
Asp Glu Glu Lys Arg Val Ala Gln Arg Ala Leu Met Gln Ser Leu
            395                 400                 405
Asn Met Leu Val Gln Thr Glu Gly Lys Glu Arg Ser Leu Gly Glu
            410                 415                 420
Tyr Gln Cys Leu Leu Glu Leu His Gly Phe His Gln Val Gln Val
            425                 430                 435
Val His Leu Gly Gly Val Leu Asp Ala Ile Leu Ala Thr Lys Val
            440                 445                 450
Ala Pro (2) INFORMATION FOR SEQ ID NO:    4:

(i) SEQUENCE CHARACTERISTICS:
        (A) LENGTH: 1516 base pairs
        (B) TYPE: nucleic acid
        (C) STRANDEDNESS: single
        (D) TOPOLOGY: linear (vii) IMMEDIATE SOURCE:
        (A) LIBRARY: LNODNOT08
        (B) CLONE: 3053783

(xi) SEQUENCE DESCRIPTION: SEQ ID NO: 4 :

TCCACAGCGG GGAGCCCATG GACAAAGCTG GCGGCTACGG GATCCAGGCC CTGGGCGGCA    60

TGCTGGTGGA GTCCGTACAC GGGGACTTTC TGAACGTGGT GGGATTCCCG CTGAACCACT   120
```

```
TCTGCAAGCA GCTGGTGAAG CTCTACTACC CGCCCCGTCC GGAGGACCTG CGGCGGAGTG      180

TCAAGCACGA CTCCATCCCG GCCGCGGACA CCTTCGAAGA CCTCAGTGAC GTGGAGGGGG      240

GTGGCTCGGA GCCCACTCAG AGGGACGCGG GCAGCCGCGA TGAGAAGGCC GAGGCGGGAG      300

AGGCGGGACA GGCCACGGCA GAGGCTGAGT GTCACAGGAC TCGGGAGACC CTGCCTCCGT      360

TCCCGACACG CCTCCTGGAG CTGATTGAGG CTTTATGCT ATCCAAGGGC CTGCTCACCG       420

CTTGCAAACT GAAGGTGTTC GATTTGTTAA AAGATGAAGC ACCCCAGAAG GCTGCGGATA      480

TTGCCAGCAA AGTGGACGCC TCTGCGTGTG GAATGGAGAG GCTTCTGGAC ATCTGTGCTG      540

CCATGGGGCT CCTGGAGAAG ACAGAGCAAG GTTACAGTAA CACAGAGACA GCGAACGTCC      600

ACCTGGCATC GGATGGCGAA TACTCTCTGC ACGGCTTCAT CATGCACAAT AATGACCTCA      660

CATGGAACCT CTTTACATAC CTGGAGTTTG CCATCCGAGA GGGAACAAAC CAGCACCACA      720

GGGCGTTGGG GAAGAAGGCG GAAGATCTGT TCCAGGATGC GTACTACCAG AGCCCGGAGA      780

CGCGGCTGAG GTTCATGCGG GCCATGCACG GCATGACGAA GCTGACTGCG TGCCAGGTGG      840

CCACGGCCTT CAATCTGTCC CGCTTCTCCT CCGCCTGCGA CGTGGGAGGC TGCACCGGTG      900

CACTGGCCCG AGAGCTGGCC CGTGAGTACC CTCGTATGCA GGTGACTGTG TTTGACCTCC      960

CAGACATTAT CGAGCTGGCC GCCCACTTCC AACCCCCCGG ACCGCAGGCA GTGCAGATCC     1020

ACTTCGCAGC AGGTGACTTT TTCAGGGACC CCCTCCCCAG CGCTGAGCTG TACGTCCTGT     1080

GCCGGATCCT GCATGACTGG CCAGACGACA AGTCCACAA GTTACTCAGC AGGGTCGCCG      1140

AGAGCTGCAA GCCAGGGGCC GGCCTGCTGC TGGTGGAGAC GCTCCTGGAT GAGGAGAAGA     1200

GGGTGGCGCA GCGCGCCCTG ATGCAGTCAC TGAACATGCT GGTGCAGACT GAAGGCAAGG     1260

AGCGGAGCCT GGGCGAGTAT CAGTGCTTGC TGGAGCTGCA CGGCTTCCAC CAGGTGCAGG     1320

TGGTGCACTT GGGGGGTGTC CTGGATGCCA TCTTGGCCAC CAAAGTGGCC CCCTGAAGCC     1380

CAGGCAGCAT GTTCATTATA GGGATGTCCT CCCCCAGGCT GCAGGTGGAC CGCCCGGTCC     1440

CCAAGTACCA TAGGACAGTC ACATAGGAGC GTGTAGTCGT GACTGAATAA AGAAAGCAAA     1500

AGCCAAAAAA AAAAAA                                                    1516

(2) INFORMATION FOR SEQ ID NO: 5:

(i) SEQUENCE CHARACTERISTICS:
        (A) LENGTH: 345 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 607854

(xi) SEQUENCE DESCRIPTION: SEQ ID NO: 5 :

Met Gly Ser Ser Glu Asp Gln Ala Tyr Arg Leu Leu Asn Asp Tyr
                 5                  10                  15

Ala Asn Gly Phe Met Val Ser Gln Val Leu Phe Ala Ala Cys Glu
                20                  25                  30

Leu Gly Val Phe Asp Leu Leu Ala Glu Ala Pro Gly Pro Leu Asp
                35                  40                  45

Val Ala Ala Val Ala Ala Gly Val Arg Ala Ser Ala His Gly Thr
                50                  55                  60

Glu Leu Leu Leu Asp Ile Cys Val Ser Leu Lys Leu Leu Lys Val
                65                  70                  75

Glu Thr Arg Gly Gly Lys Ala Phe Tyr Arg Asn Thr Glu Leu Ser
```

-continued

```
                    80                    85                    90
Ser Asp Tyr Leu Thr Thr Val Ser Pro Thr Ser Gln Cys Ser Met
                        95                   100                   105
Leu Lys Tyr Met Gly Arg Thr Ser Tyr Arg Cys Trp Gly His Leu
                110                   115                   120
Ala Asp Ala Val Arg Glu Gly Arg Asn Gln Tyr Leu Glu Thr Phe
                125                   130                   135
Gly Val Pro Ala Glu Glu Leu Phe Thr Ala Ile Tyr Arg Ser Glu
                140                   145                   150
Gly Glu Arg Leu Gln Phe Met Gln Ala Leu Gln Glu Val Trp Ser
                155                   160                   165
Val Asn Gly Arg Ser Val Leu Thr Ala Phe Asp Leu Ser Val Phe
                170                   175                   180
Pro Leu Met Cys Asp Leu Gly Gly Ala Gly Ala Leu Ala Lys
                185                   190                   195
Glu Cys Met Ser Leu Tyr Pro Gly Cys Lys Ile Thr Val Phe Asp
                200                   205                   210
Ile Pro Glu Val Val Trp Thr Ala Lys Gln His Phe Ser Phe Gln
                215                   220                   225
Glu Glu Glu Gln Ile Asp Phe Gln Glu Gly Asp Phe Phe Lys Asp
                230                   235                   240
Pro Leu Pro Glu Ala Asp Leu Tyr Ile Leu Ala Arg Val Leu His
                245                   250                   255
Asp Trp Ala Asp Gly Lys Cys Ser His Leu Leu Glu Arg Ile Tyr
                260                   265                   270
His Thr Cys Lys Pro Gly Gly Gly Ile Leu Val Ile Glu Ser Leu
                275                   280                   285
Leu Asp Glu Asp Arg Arg Gly Pro Leu Leu Thr Gln Leu Tyr Ser
                290                   295                   300
Leu Asn Met Leu Val Gln Thr Glu Gly Gln Glu Arg Thr Pro Thr
                305                   310                   315
His Tyr His Met Leu Leu Ser Ser Ala Gly Phe Arg Asp Phe Gln
                320                   325                   330
Phe Lys Lys Thr Gly Ala Ile Tyr Asp Ala Ile Leu Ala Arg Lys
                335                   340                   345
```